US006332093B1

(12) United States Patent
Painchaud et al.

(10) Patent No.: US 6,332,093 B1
(45) Date of Patent: Dec. 18, 2001

(54) SCANNING MODULE FOR IMAGING THROUGH SCATTERING MEDIA

(75) Inventors: Yves Painchaud, Sainte-Marie; Alain Mailloux, Quebec, both of (CA)

(73) Assignee: Art Recherches et Technologies Avancees Inc./Art Advanced Research Technologies, Inc., Ville Saint-Laurent (CA)

(*) Notice: Subject to any disclaimer, the term of this patent is extended or adjusted under 35 U.S.C. 154(b) by 0 days.

(21) Appl. No.: 09/129,886

(22) Filed: Aug. 6, 1998

(51) Int. Cl.[7] .................................................. A61B 6/00
(52) U.S. Cl. .................................. 600/476; 356/342
(58) Field of Search .......................... 600/473, 476, 600/310; 356/337, 338, 342, 345; 250/339.11

(56) References Cited

U.S. PATENT DOCUMENTS

| 4,570,638 | * | 2/1986 | Stoddart et al. . |
|---|---|---|---|
| 4,807,637 | * | 2/1989 | Bjorkholm . |
| 4,810,875 | * | 3/1989 | Wyatt . |
| 4,945,239 | | 7/1990 | Wist et al. . |
| 5,137,355 | | 8/1992 | Barbour et al. . |
| 5,293,873 | | 3/1994 | Fang . |
| 5,353,799 | | 10/1994 | Chance . |
| 5,371,368 | | 12/1994 | Alfano et al. . |
| 5,386,827 | | 2/1995 | Chance et al. . |
| 5,413,098 | | 5/1995 | Benaron . |
| 5,424,843 | | 6/1995 | Tromberg et al. . |
| 5,427,094 | | 6/1995 | Thurston et al. . |
| 5,427,095 | | 6/1995 | Thurston et al. . |
| 5,441,054 | | 8/1995 | Tsuchiya . |
| 5,529,065 | | 6/1996 | Tsuchiya . |
| 5,555,885 | | 9/1996 | Chance . |
| 5,582,169 | | 12/1996 | Oda et al. . |
| 5,625,458 | | 4/1997 | Alfano et al. . |
| 5,630,423 | | 5/1997 | Wang et al. . |
| 5,640,247 | | 6/1997 | Tsuchiya et al. . |
| 5,676,142 | | 10/1997 | Miwa et al. . |
| 5,694,931 | | 12/1997 | Tsuchiya . |
| 5,694,938 | | 12/1997 | Feng et al. . |
| 5,703,923 | * | 12/1997 | Bardash . |
| 5,719,398 | | 2/1998 | Colak . |
| 5,758,653 | | 6/1998 | Schotland . |
| 6,091,983 | * | 7/2000 | Alfano et al. . |

FOREIGN PATENT DOCUMENTS 0 633 527 A1   7/1993  (EP) .

OTHER PUBLICATIONS

"Time Resolved Reflectance and Transmittance for the Non– invasive Measurement of Tissue Optical Properties"; Michael Patterson, B. Chance and B.C. Wilson; Applied Optics, vol. 28, No. 12, Jun. 15, 1989, pp. 2331–2336.
"Enhanced time–resolved imaging with a diffusion model of photon transport.", Optics Letters, vol. 19, No. 5, Mar. 1, 1994, pp. 311–313.

* cited by examiner

*Primary Examiner*—Marvin M. Lateef
*Assistant Examiner*—Shawna J Shaw
(74) *Attorney, Agent, or Firm*—James Anglehart; Stewart L. Gitler (57) ABSTRACT

A scanning module for imaging through scattering media is provided. The scanning module image through scattering media while alleviating adverse effects of the weak transmission through highly scattering media. The injection of photons is optimized so that the overall transmission is increased compared to the conventional art. Cross-talk effects in a multi-port geometry are eliminated thereby increasing parallelism.

24 Claims, 7 Drawing Sheets

Injection of photons at the input surface using re-injection.

Figure 1: Scanning system for imaging through scattering media.

Figure 6: Parallel scanning process using 4 ports.

Fig. 11

Figure 2: Theoretical temporal distribution of the spatially-integrated transmission.

Figure 3: Theoretical spatial distribution of the time-integrated transmission.

Figure 4: Theoretical temporal distribution of the spatially-integrated reflection.

Figure 5: Theoretical spatial distribution of the time-integrated reflection.

Figure 7: Injection of photons at the input surface (without re-injection).

Figure 8: Injection of photons at the input surface using re-injection.

Figure 9: Gain of input re-injection as a function of the slab thickness.

Figure 10: Gain of input re-injection as a function of the absorption coefficient.

Figure 12: Optimized light collection using a re-injection reflector.

Figure 13: Example of two-ports geometry using optical fibers.

Figure 14: Example of cross-talk effects on detected signal in a two-ports geometry.

Figure 15: Two-ports geometry using optical fibers of adjusted length.

Figure 16: Detected signals at port 1 (a) and port 2 (b) in a two-ports geometry using optical fibers of adjusted lengths.

SCANNING MODULE FOR IMAGING THROUGH SCATTERING MEDIA

BACKGROUND OF THE INVENTION

1. Field of the Invention

The present invention relates to a scanning module for imaging through scattering media. More particularly, the present invention is directed to a scanning module for imaging through scattering media while alleviating adverse effects of the weak transmission through highly scattering media. According to the present invention the injection of photons is optimized so that the overall transmission is increased compared to the conventional art. In addition, the present invention eliminates cross-talk effects in a multi-port geometry thereby increasing parallelism.

2. Background of the Invention

Infrared imaging through scattering media is an area of research that has created enormous interest. A main target application is breast cancer detection, in which the use of a near infrared short-pulse laser is particularly appropriate. Obtaining images of the interior of the breast is complicated by the extensive scattering of light in such a medium. The scattering property of the breast causes a weak transmission through a thick slab and blurring of the image obtained from the transmitted light. The use of ultra-short laser pulses combined with an ultra-fast and ultra-sensitive detection system reduces the adverse effects of scattering.

The trajectory of a photon propagating inside a scattering medium can be predicted only on a statistical basis. In addition to the probability of being absorbed, the photons are subject to numerous scattering events. In a slab medium that is highly scattering and weakly absorbing, such as the human breast, most photons are reflected toward the entrance surface after traveling only a few millimeters into the tissue. Other photons are absorbed by the medium or transmitted to the output surface where they can be detected. In the case of typical breast thickness and optical parameters, 0.001 to 1% of the injected photons are transmitted to the output surface.

Figure 1:
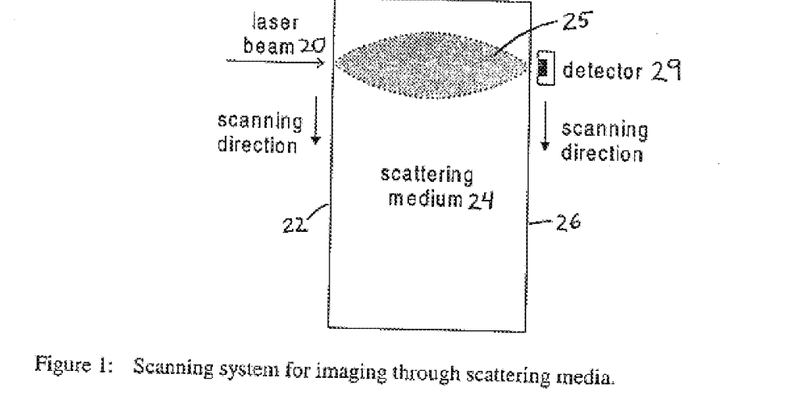
FIG. 1 is a schematic view of a scanning system through a scattering medium as known in the prior art.

The light transmitted to the output surface carry the most significant information about the interior of the medium, since the reflected light carry information predominantly from a region close to the input surface. In previous systems as shown in FIG. 1, images of the interior of a scattering medium 24, such as the human breast, have been obtained by scanning a laser beam 20 of small diameter along the input surface 22 and detecting light emerging from a small area along the output surface 26. The grey region 25 indicated in the dotted line in FIG. 1 illustrates the region through which the photons pass when traveling from the injected point to detector 29. As discussed previously, such an imaging technique is complicated by the strong scattering property of the medium: the number of transmitted photons is very weak compared to the number of injected photons and the scattering causes a strong blurring of the image. There is a need for developing techniques that alleviate the blurring and the weak transmission associated with the scattering.

Referring to FIG. 1, when a single photon is injected at the input surface 22 of a scattering slab 24, it has a certain probability to be transmitted to the opposite surface 26 at some point and after some traveling time. Similarly, when injecting an infinitely short light pulse at the input surface 22, a certain proportion of light (typically weak) is transmitted. The transmitted light can then be collected over a certain spatial region of the output surface and during a certain time interval. In other words, when arriving at the output surface 26, the input pulse is spread spatially and temporally forming a spatio-temporal distribution of the transmitted light.

Figure 2:
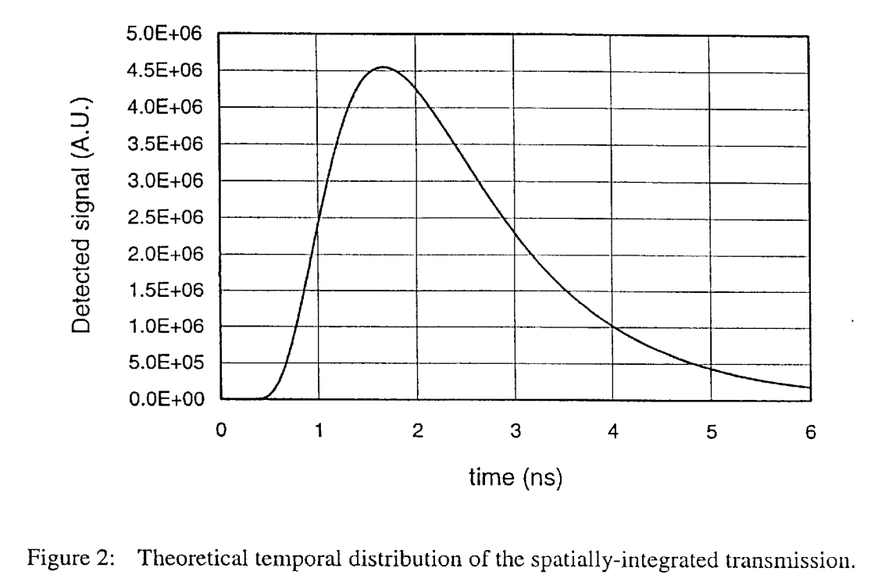
FIG. 2 is a graph representing theoretical temporal distribution of a spatially-integrated transmission.
Figure 3:
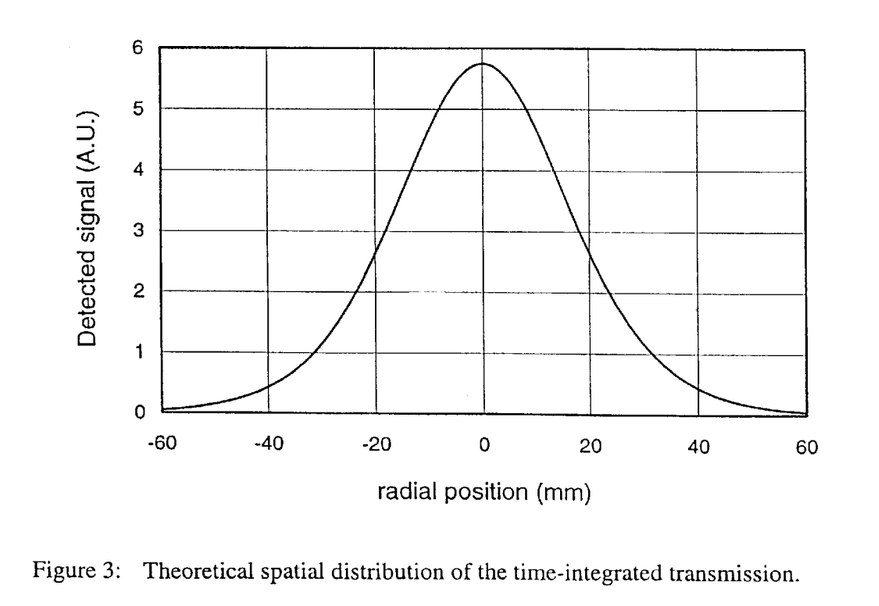
FIG. 3 is a graph representing theoretical spatial distribution of a time-integrated transmission.

Theoretical expressions (the diffusion model) allow to correctly predict the spatio-temporal distribution of the emerging light from the output surface corresponding to the injection of an ultra-short light pulse at the input surface of a homogeneous scattering slab. FIGS. 2 and 3 illustrate examples of the theoretical temporal and spatial distributions of the transmitted light in the case of a 40 mm thick scattering slab having a scattering coefficient $\mu_s'=1$ mm$^{-1}$, an absorption coefficient $\mu_a=0.002$ mm$^{-1}$ and a refractive index n=1.34. The scattering coefficient $\mu_s'$ is the probability of the photon being isotropically scattered per infinitesimal pathlength, and the absorption coefficient $\mu_a$ is the probability of the photon being absorbed per infinitesimal pathlength. FIG. 2 shows the temporal distribution of the spatially-integrated transmission, and FIG. 3 shows the spatial distribution of the time-integrated transmission. In FIG. 2, the time origin corresponds to the entry of the light pulse in the medium. In FIG. 3, the radial position 0 corresponds to the point of the output surface facing the injection point of the input surface. As can be seen in this particular case, the part of the input pulse that reaches the output surface emerges into a 40 mm Gaussian spot temporally spread during a time interval of about 5 ns.

Similar to the transmission mechanism, when a single photon is injected at the input surface of a scattering slab, it has a certain probability of being reflected back to the input surface at some point and after some travel time. When injecting an infinitely short pulse at the input surface, a certain proportion of light (typically very high) is reflected. The reflected light can then be collected over a certain spatial region of the input surface and during a certain time interval. In other words, the reflected pulse is spread spatially and temporally forming a spatio-temporal distribution of the reflected light.

Figure 4:
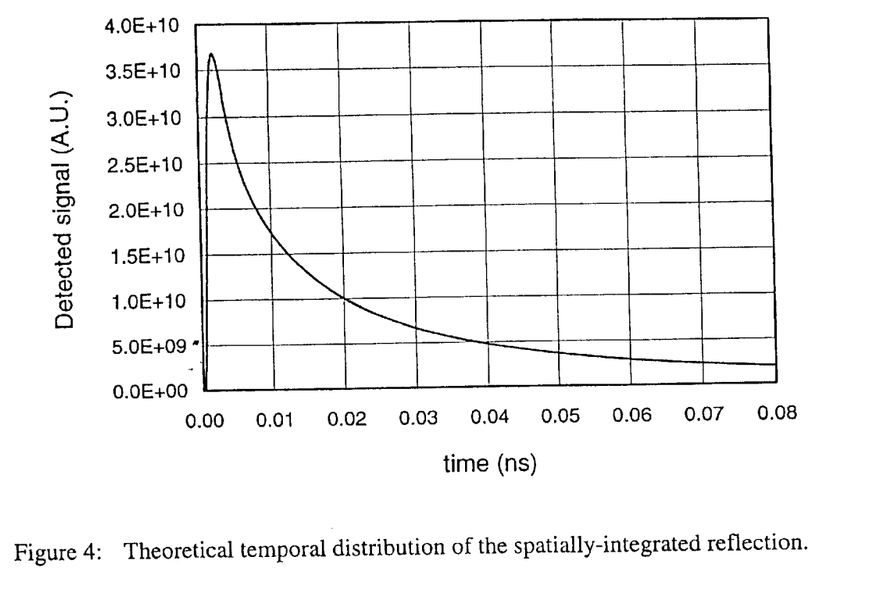
FIG. 4 is a graph representing theoretical temporal distribution of a spatially-integrated reflection.
Figure 5:
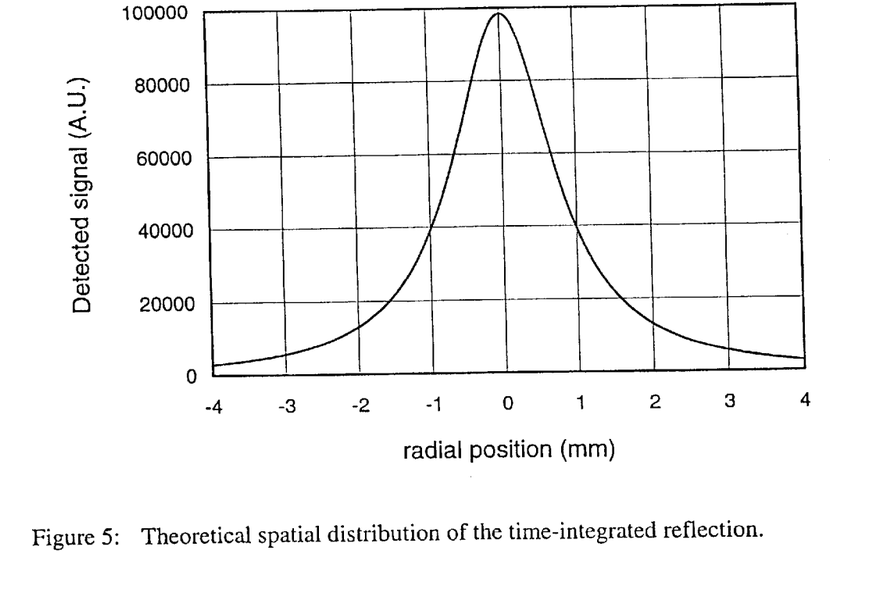
FIG. 5 is a graph representing theoretical spatial distribution of a time-integrated reflection.

Again, the diffusion model provides theoretical expressions for the spatio-temporal distribution of the emerging light from the input surface corresponding to the injection of an ultra-short light pulse at the input surface of a homogeneous scattering slab. FIGS. 4 and 5 show examples of the theoretical temporal and spatial distributions of the reflected light in the case of a 40 mm thick scattering slab having a scattering coefficient $\mu_s'=1$ mm$^{-1}$, an absorption coefficient $\mu_a=0.002$ mm$^{-1}$ and a refractive index n=1.34. FIG. 4 shows the temporal distribution of the spatially-integrated reflection and FIG. 5 shows the spatial distribution of the time-integrated reflection. In FIG. 4, the time origin corresponds to the entry of the light pulse in the medium, and in FIG. 5, the radial position 0 corresponds to the injection point. As can be seen for this particular case, the part of the input pulse that is reflected back emerges into a 2 mm Gaussian spot temporally spread during a time interval of about 50 ps.

Figure 6:
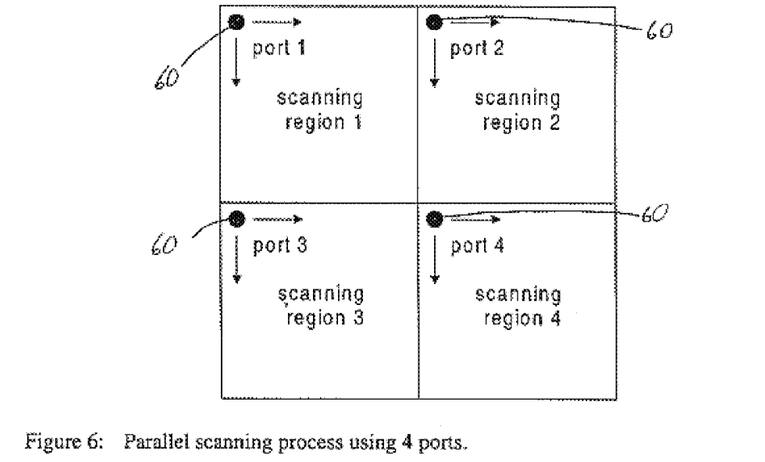
FIG. 6 is a depiction of a parallel scanning process utilizing four ports.

The scanning process illustrated in FIG. 1 is typically slow due to the weak number of transmitted photons and the typically required averaging. One way to achieve a faster scan is to use parallelism, that is a duplication of the scanning process in many ports 60, as illustrated in FIG. 6. Each port 60 performs a scan over a reduced region allowing for a faster process. As far as possible, the different ports 60 must be independent and thus the spacing between two adjacent ports must be sufficiently large to avoid cross-talk effects. The cross-talk (interaction between ports) is superimposed on the useful signal (the light traveling from the input to the output of a single port). The larger the port spacing, the weaker the cross-talk will be, but the larger the scanned region for each port 60. As a result, there is a trade-off between the cross-talk and the scanning speed. For the particular case of FIG. 3, to avoid significant cross-talk, the port spacing must be about 40 mm. In general cases, the port spacing must be approximately equal to the scattering slab thickness.

The use of optical fibers to carry light is appropriate for the present application, especially when parallelism is used. All-fiber dividers (couplers) are available allowing for an easy separation of a main laser beam into many ports. Furthermore, the light is brought close to the medium and collecting fibers can be used allowing for a safe an efficient scanner.

SUMMARY OF THE INVENTION

These and other deficiencies of the prior art are addressed by the present invention which is directed to a scanning module for imaging through scattering media while alleviating adverse effects of the weak transmission through highly scattering media.

An object of the present invention is to provide an apparatus for optimizing the injection of light such that the overall transmission is increased compared to the conventional art.

Another object of the invention is to provide an apparatus for eliminating cross-talk effects in a multi-port geometry for an increase in parallelism.

BRIEF DESCRIPTION OF THE DRAWINGS

These and other attributes of the present invention will be described with respect to the following drawings in which.

DETAILED DESCRIPTION OF THE INVENTION

Figure 7:
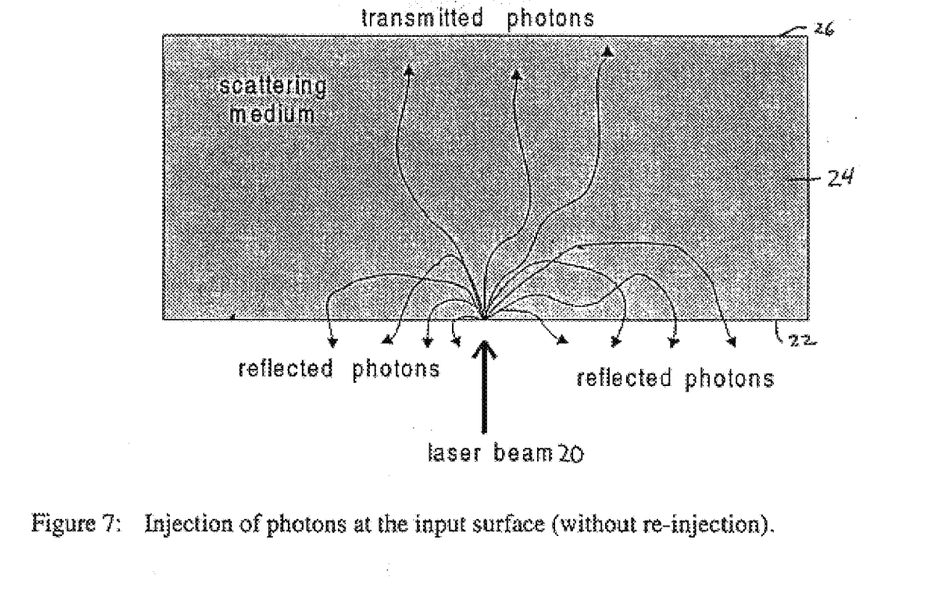
FIG. 7 is a diagram illustrating the trajectories of transmitted and reflected photons in a scattering medium resulting from the injection of photons at an input surface.
Figure 8:
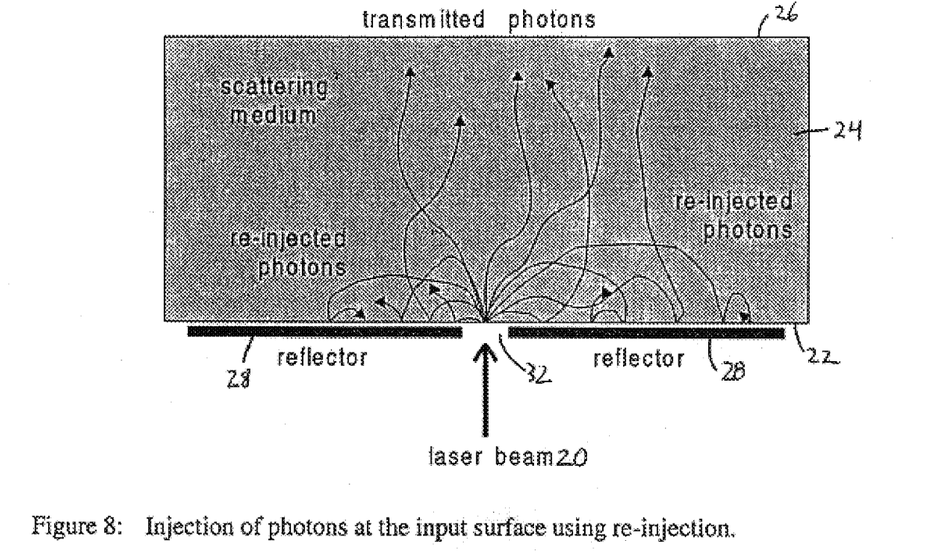
FIG. 8 is a diagram illustrating the trajectories of transmitted and reflected photons in a scattering medium resulting from the injection of photons at an input surface using a re-injection reflector according to the present invention.

As discussed previously, most of the photons injected into a scattering medium 24 are reflected back to the input surface 22 after traveling only a few millimeters in the medium 24. Referring to FIG. 7, a reflected photon exits the medium 24 and has no chance to contribute to the detected signal at the output surface 26. Nevertheless, referring to FIG. 8, if the photons hit a reflector 28, they will be reflected back into the scattering medium 30, having a certain probability of reaching the output surface 26 and contributing to the detected signal. The employment of such reflectors 28 can be used to significantly improve the overall transmission. Furthermore, referring to FIGS. 2–5, it is apparent that the reflection process is fast and covers a small area compared to the transmission process. Therefore, re-injected photons will contribute to the transmission without significantly changing the spatio-temporal distribution of the transmission.

It should be noted that such reflection naturally occurs partially due to the Fresnel reflection between the scattering medium and the external medium, since most of the time, an index mismatch exists.

Figure 9:
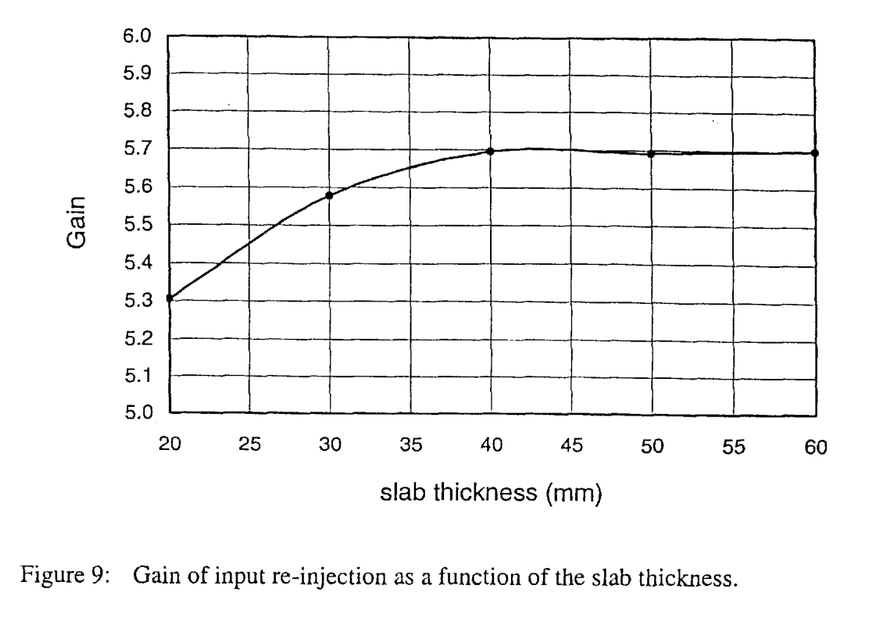
FIG. 9 is a graph showing the gain of input re-injection as a function of the slab thickness, according to the present invention.

Assuming that the laser beam 20 is introduced into the scattering medium 24 by traversing an infinitely large reflector 28 through a hole 32 of negligible dimension, the gain in the total transmission can be calculated using Monte Carlo simulations. FIG. 9 shows the total gain of input re-injection as a function of slab thickness for a scattering medium having a scattering coefficient $\mu_s'=1$ mm$^{-1}$, an absorption coefficient $\mu_a=0.002$ mm$^{-1}$ and a refractive index n=1.34. The points in FIG. 9 represent the calculated values.

Figure 10:
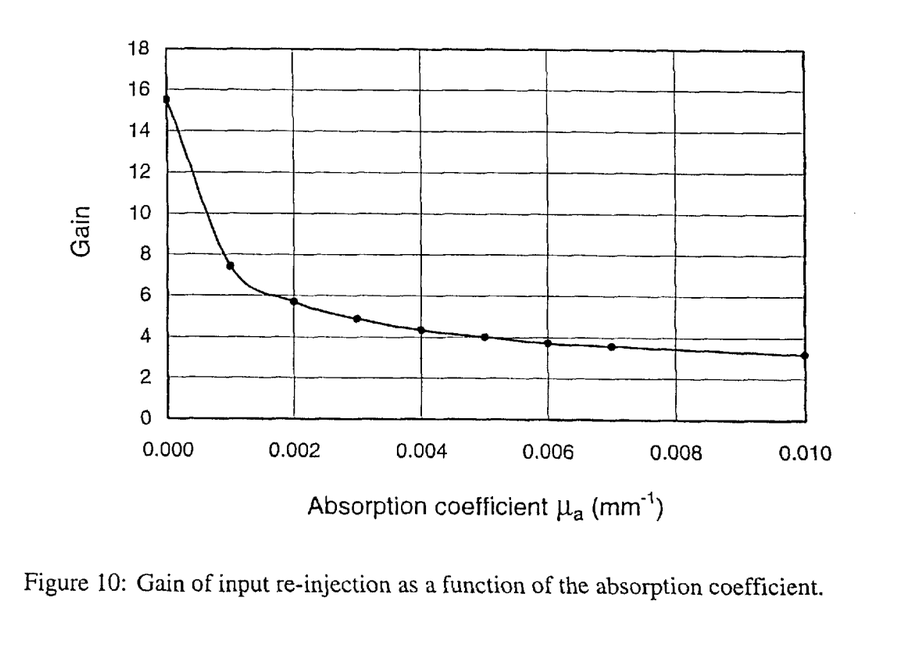
FIG. 10 is a graph showing the gain of input re-injection as a function of the absorption coefficient according to the present invention.

FIG. 10 shows the gain of input re-injection as a function of the absorption coefficient for a 40 mm thick slab having a scattering coefficient $\mu_s'=1$ mm$^{-1}$ and a refractive index n=1.34. Again, the calculations are represented by points. From the forgoing it is found that the gain of input re-injection depends significantly only on the absorption coefficient since the dependency upon the slab thickness is very weak. It can be shown that the gain dependency upon the scattering coefficient is very similar to the dependency upon the slab thickness. For weakly absorbing media, such as the human breast, input re-injection could result in an increase of the transmission by approximately a factor of five.

Figure 11:
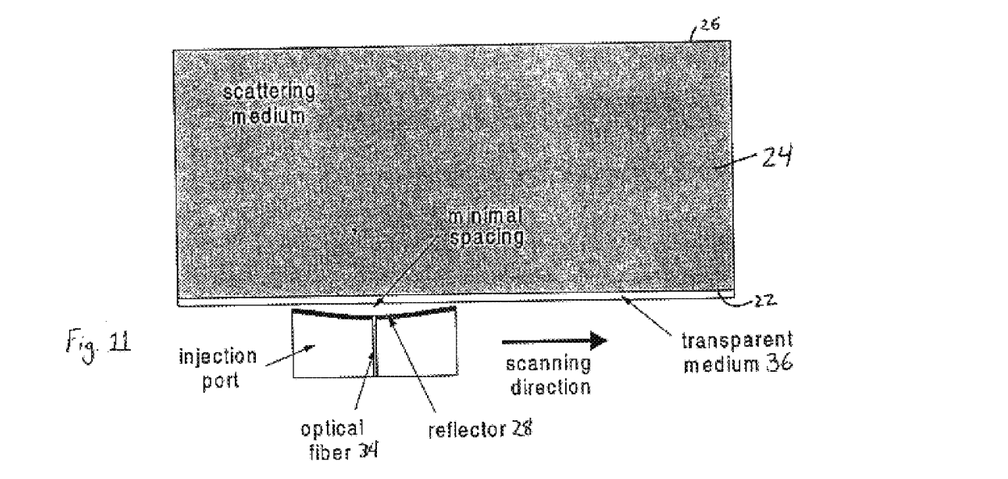
FIG. 11 is a diagram showing optimized injection using an optical fiber and re-injection reflector according to the present invention.

The most important factor, in order to take advantage of re-injection, is to introduce the laser beam 20 through a hole 32 in the reflector 28 that is as small as possible. Such an injection can be easily achieved using an optical fiber 34 as illustrated in FIG. 11. Most of the time, a transparent medium 36 must be used between the scattering medium 24 and the external medium (typically air) mainly in order to maintain the slab shape when the scattering medium is soft or liquid. Such a transparent medium 36 must be as thin as possible in order to avoid delays that could change the time-dependent transmission. Nevertheless, a minimal spacing between the optical fiber 34 and the scattering medium 24 of approximately 2 mm is beneficial to avoid too high an intensity of the laser beam 20 for applications such as breast optical scanning.

Considering FIG. 5, the size of the reflector 28 can be limited to approximately 5 mm in diameter. A larger reflector 28 would increase transmission only slightly and the additional detected photons would be less interesting as they would come from a source point much farther from the injection point and would be detected with larger time delays.

Figure 12:
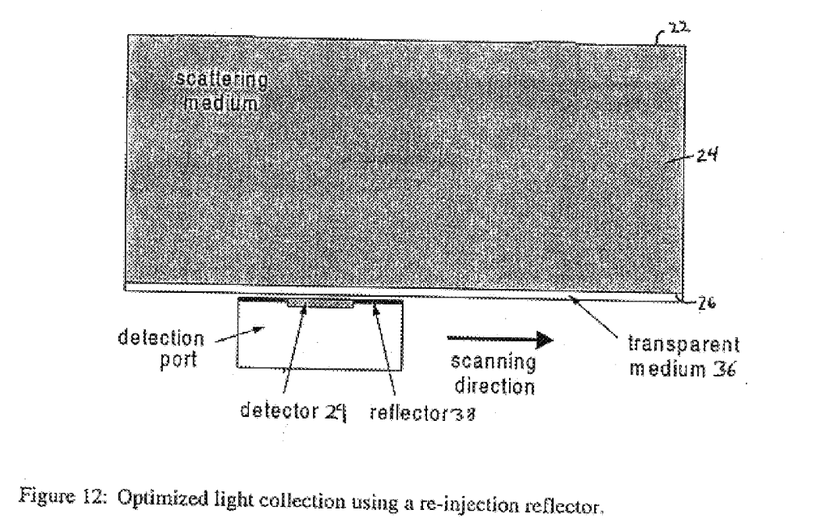
FIG. 12 is a diagram showing an optimized light collection arrangement using a re-injection reflector according to the present invention.

In the case of a detection limited to a small area, the same re-injection strategy can be used, as illustrated in FIG. 12. The use of a doughnut shaped re-injection reflector 38 increases the effective surface of the detector. The effective detection surface is not equal to the reflector diameter since the probability of a re-injected photon reaching the detector is not equal to one. The re-injection reflector 38 will increase the number of detected photons but will also contribute to a slight degradation of the image resolution. There is thus a trade-off between the increase in the detected light and the decrease in the image quality. The benefit of a re-injection reflector 38 at the output is strongly dependent on the intrinsic detected area. The smaller the detector is, the higher the gain from using the re-injection reflector will be.

Figure 13:
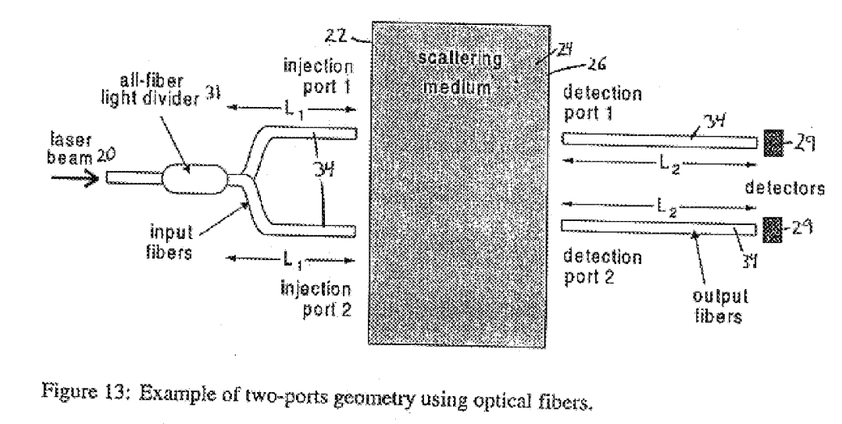
FIG. 13 is a diagram showing a usual two-port geometry using optical fibers.

As discussed previously, another way to alleviate weak transmission of light is to use parallelism. Parallelism is complicated by the cross-talk that exists between the different ports in a multi-port geometry. FIG. 13 shows an example of a two-port geometry using optical fibers 34, and FIG. 14 shows the corresponding cross-talk effects on the detected signals.

The laser beam 20 enters an all-fiber light divider 31 which divides the laser beam into input optical fibers 34, which are fed to port 1 and port 2. Optical fibers 34 transmit the received light to the detectors 29.

Figure 14:
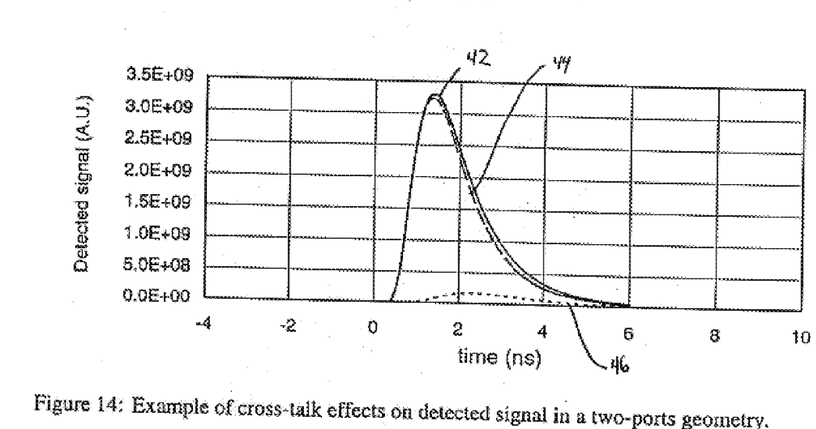
FIG. 14 is a graph showing cross-talk effects on a detected signal in a two port geometry.

In the example shown in FIG. 14, theoretical calculations are given for a 40 mm thick slab having a scattering coefficient $\mu_s'=1$ mm$^{-1}$, an absorption coefficient $\mu_a=0.002$ mm$^{-1}$ and a refractive index n=1.34, the port separation is 40 mm. The calculation corresponds to the total temporal distribution of the transmission over a small area (solid line) 42 which is the sum of the useful signal (dashed line) 44 and cross-talk (dotted line) 46. The cross-talk limits the spacing between two adjacent ports to about a separation equal to the thickness of the scattering slab.

In a multi-port scanning device as illustrated in FIG. 13, time dependent transmissions through the different ports can be measured together and at the same time using a fast detecting system such as a streak camera. Most of the time, it is useful to adjust the fiber lengths $L_1$ and $L_2$ of the different ports to equal sizes so that the different light signals are synchronized and arrive simultaneously at the detectors 29.

Figure 15:
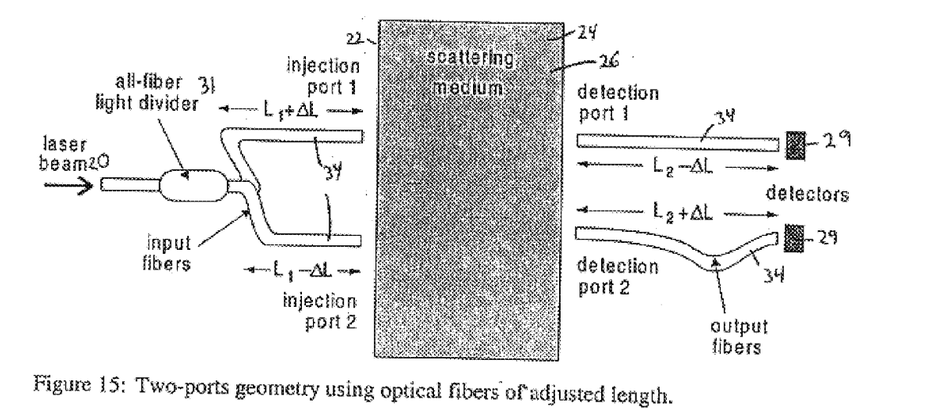
FIG. 15 is a diagram showing a two-port geometry using optical fibers of adjusted length according to the present invention.
Figure 16:
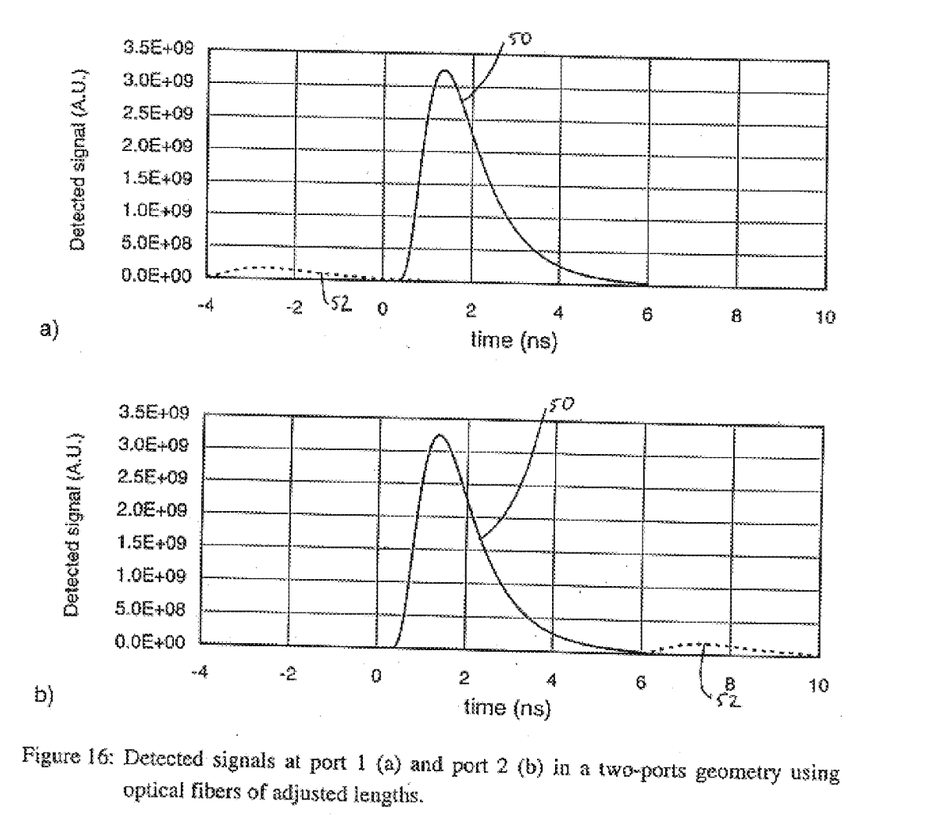
FIGS. 16a and 16b are graphs of detected signals at ports 1 and 2 in a two-port geometry using optical fibers of adjusted length, as shown in FIG. 15, according to the present invention.

Another strategy can be used to synchronize the useful signals while eliminating the cross-talk. The strategy is to use unequal pathlengths at both the input and output side of the medium 24 as illustrated in FIG. 15. FIG. 16 shows the detected signals corresponding to FIG. 15. The useful signals are shown in solid line 50 while the cross-talks are shown in dotted lines 52. Once again the theoretical calculations are given for a 40 mm thick slab having a scattering coefficient $\mu_s'=1$ mm$^{-1}$, an absorption coefficient $\mu_a=0.002$ mm$^{-1}$ and a refractive index n=1.34, the port separation is 40 mm and the fiber length difference ΔL is 50 cm. FIG. 16a shows the signal detected at port 1 and FIG. 16b shows the signal detected at port 2.

As can be seen in FIGS. 16a and 16b, the two useful signals arrive at the detector simultaneously since the light travels along the same total length of fiber $L_1+L_2$. The cross-talk arrive at the detector before or after the useful signal: the cross-talk from port 2 to port 1 travels along a length of fiber equal to $L_1+L_2-2\Delta L$ and the cross-talk from port 1 to port 2 travels along a length of fiber equal to $L_1+L_2+2\Delta L$. Using this strategy, it is possible to eliminate the cross-talk since it is not temporally superimposed on the useful signal. Such a strategy can be used only if the repetition rate of the input pulses is sufficiently low: the time interval between the time windows at which the useful signal occurs must be sufficiently large to accommodate the delayed cross-talks.

The same strategy can also be applied to multi-port geometries that contain more than two ports. Different pathlengths must then be used with always the same goal of keeping the same total pathlength (input and output fibers) for the useful signals while having different pathlengths for the cross-talks.

Using the foregoing strategy to eliminate the cross-talk makes it possible to relax the constraint for the scanning configuration. The multi-port geometry discussed previously is limited by the cross-talk effects. If the cross-talk is eliminated, any kind of parallelism can be used and adjacent ports can be as close as desired. The scanning area of each port is not limited anymore by the minimal fiber spacing and more dense parallelism can be used.

Having described several embodiments of the scanning module for imaging through scattering media in accordance with the present invention, it is believed that other modifications, variations and changes will be suggested to those skilled in the art in view of the description set forth above. It is therefor to be understood that all such variations, modifications and changes are believed to fall within the scope of the invention as defined in the appended claims.

What is claimed is:

1. An apparatus for imaging through scattering media, comprising:
    an ultra short light pulse source disposed on a first side of said scattering media;
    at least one detector disposed on a second side of said scattering media; and
    a reflector disposed adjacent to said first side of said scattering media to reflect back into said scattering media part of photons injected into said scattering media from said ultra short light pulse source;
    said part of photons being reflected back to said first side of said scattering media by scattering;
    wherein said ultra short light pulse is transmitted into said scattering media through a hole in said reflector, and said at least one detector receives light transmitted through said scattering media from said source.

2. An apparatus for imaging through scattering media as recited in claim 1, further comprising an optical fiber for carrying said ultra short light pulse from said source to said first side of said scattering media through said reflector.

3. An apparatus for imaging through scattering media as recited in claim 2, wherein said source moves in a scanning direction perpendicular to said first side of said scattering media.

4. An apparatus for imaging through scattering media as recited in claim 3, wherein said detector moves in a direction parallel to said scanning direction.

5. An apparatus for imaging through scattering media as recited in claim 1, further comprising a transparent medium disposed on said first side of said scattering media to maintain a shape of said scattering media.

6. An apparatus for imaging through scattering media as recited in claim 1, wherein said source moves in a scanning direction perpendicular to said first side of said scattering media.

7. An apparatus for imaging through scattering media as recited in claim 6, wherein said detector moves in a direction parallel to said scanning direction.

8. An apparatus for imaging through scattering media as recited in claim 1, further comprising a circular re-injection reflector disposed around said detector to increase an effective surface of said detector.

9. An apparatus for imaging through scattering media as recited in claim 1, further comprising a transparent medium disposed on said second side of said scattering media to maintain a shape of said scattering media.

10. An apparatus for imaging through scattering media, comprising:
    an ultra short light pulse source disposed on a first side of said scattering media;
    at least one detector disposed on a second side of said scattering media; and
    a circular re-injection reflector disposed around said at least one detector to increase an effective surface of said at least one detector.

11. An apparatus for imaging through scattering media as recited in claim 10, further comprising an optical fiber for carrying said ultra short light pulse from said source to said first side of said scattering media.

12. An apparatus for imaging through scattering media as recited in claim 11, wherein said source moves in a scanning direction perpendicular to said first side of said scattering media.

13. An apparatus for imaging through scattering media as recited in claim 12, wherein said detector moves in a direction parallel to said scanning direction.

14. An apparatus for imaging through scattering media as recited in claim 10, further comprising a transparent medium disposed on said first side of said scattering media to maintain a shape of said scattering media.

15. An apparatus for imaging through scattering media as recited in claim 10, wherein said source moves in a scanning direction perpendicular to said first side of said scattering media.

16. An apparatus for imaging through scattering media as recited in claim 15, wherein said detector moves in a direction parallel to said scanning direction.

17. An apparatus for imaging through scattering media as recited in claim 10, further comprising a transparent medium disposed on said second side of said scattering media to maintain a shape of said scattering media.

18. An apparatus for imaging through scattering media, comprising:
    an ultra short light pulse source disposed on a first side of said scattering media;
    at least two detectors disposed on a second side of said scattering media;
    a divider which splits said ultra short light pulse into at least two equal optical pulses;
    at least two first optical fibers, disposed between said divider and said scattering media, said at least two optical fibers receiving and transmitting said at least two optical pulses to said scattering media; and
    at least two second optical fiber s disposed on said second side of said scattering media for transmitting said received light to said at least two detectors, wherein any cross-talk arrives at said at least two detectors before or after two useful signals from said two first optical fibers.

19. An apparatus for imaging through scattering media as recited in claim 18, wherein a length of a first one of said first optical fibers plus a length of a first one of said second optical fibers is equal to a length of a second one of said first optical fibers plus a length of a second one of said second optical fibers.

20. An apparatus for imaging through scattering media as recited in claim 19, wherein said at least two first optical fibers are of unequal length, and said at least two second optical fibers are of unequal length.

21. An apparatus for imaging through scattering media as recited in claim 18, wherein a repetition rate of said ultra short pulses is small so that time intervals between said ultra short pulses are large enough to accommodate delayed cross-talk.

22. An apparatus for imaging through scattering media as recited in claim 18, wherein a first total pathlength comprising a first one of said at least two first optical fibers and a first one of said at least two second optical fibers is equal to a second total pathlength comprising a second one of said at least two first optical fibers and a second one of said at least two second optical fibers for useful signals.

23. An apparatus for imaging through scattering media as recited in claim 22, wherein cross-talk arrives at said at least to detectors before or after two useful signals from said two first optical fibers.

24. An apparatus for imaging through scattering media, comprising:
    an ultra short light pulse source disposed on a first side of said scattering media;
    at least two detectors disposed on a second side of said scattering media, said second side being opposite said first side;
    a reflector disposed adjacent to said first side of said scattering media to reflect back into said scattering media part of photons injected into said scattering media from said ultra short light pulse source;
    said part of photons being reflected back to said first side of said scattering media by scattering;
    wherein said ultra short light pulse is transmitted into said scattering media through a hole in said reflector, and said at least two detectors receive light transmitted through said scattering media from said source;
    an optical fiber for carrying said ultra short light pulse from said source to said first side of said scattering media;
    a transparent medium disposed on said first side of said scattering media to maintain a shape of said scattering media, and a transparent medium disposed on said second side of said scattering media to maintain a shape of said scattering media; and
    a circular re-injection reflector disposed around said detector to increase an effective surface of said at least two detectors;
    a divider which splits said ultra short light pulse into at least two equal optical pulses;
    at least two first optical fibers, disposed between said divider and said scattering media, said at least two optical fibers receiving and transmitting said at least two optical pulses to said scattering media; and
    at least two second optical fibers disposed on said second side of said scattering media for transmitting said received light to said at least two detectors;

wherein said source moves in a scanning direction perpendicular to said first side of said scattering media, and said detector moves in a direction parallel to said scanning direction wherein a length of a first one of said first optical fibers plus a length of a first one of said second optical fibers is equal to a length of a second one of said first optical fibers plus a length of a second one of said second optical fibers, and wherein said at least two first optical fibers are of unequal length, and said at least two second optical fibers are of unequal length.

* * * * *